US005616621A

United States Patent [19]
Popli et al.

[11] Patent Number: 5,616,621
[45] Date of Patent: Apr. 1, 1997

[54] TASTE MASKING LIQUIDS

[75] Inventors: Shankar D. Popli, Marlton; Zenaida O. Go, Hammonton, both of N.J.

[73] Assignee: American Home Products Corporation, Madison, N.J.

[21] Appl. No.: 380,540

[22] Filed: Jan. 30, 1995

[51] Int. Cl.$^6$ .................................................. A61K 47/32
[52] U.S. Cl. ...................... 514/772.4; 424/440; 424/441; 424/451; 424/465
[58] Field of Search ................... 514/772.4; 424/440, 424/441, 451, 465

[56] References Cited

U.S. PATENT DOCUMENTS

| | | | |
|---|---|---|---|
| 3,449,498 | 6/1969 | De Stevens | 424/454 |
| 4,453,979 | 6/1984 | DeMasi et al. | 106/188 |
| 4,778,676 | 10/1988 | Yang et al. | 424/78.12 |
| 4,879,108 | 11/1989 | Yang et al. | 424/440 |
| 4,882,152 | 11/1989 | Yang et al. | 424/440 |
| 4,882,153 | 11/1989 | Yang et al. | 424/440 |
| 4,882,154 | 11/1989 | Yang et al. | 424/440 |
| 4,882,155 | 11/1989 | Yang et al. | 424/440 |
| 4,882,156 | 11/1989 | Yang et al. | 424/440 |
| 4,882,157 | 11/1989 | Yang et al. | 424/440 |
| 4,882,158 | 11/1989 | Yang et al. | 424/440 |
| 4,882,159 | 11/1989 | Yang et al. | 424/440 |
| 5,183,829 | 2/1993 | Caldwell | 514/570 |
| 5,194,464 | 3/1993 | Itoh et al. | 524/42 |
| 5,260,073 | 11/1993 | Phipps | 424/465 |

FOREIGN PATENT DOCUMENTS

0614659A2  9/1994  European Pat. Off. .

OTHER PUBLICATIONS

Lioy, World Patent Abstract of JP84–247623, 1986.
Dow Chem, World Patent Abstract of AU8825946, 1989.
Raghunathan et al., *J. Pharm. Sci:*, 70(4), 1981, pp. 379–384.
Physicians' Desk Reference for Nonprescription Drugs, 15th Edition (1994) pp. 593, 594, 666 and 667, Ronald Arky et al.
Wong et al., *Chemical Abstracts*, vol. 116, #11236 (1991).
Calancki et al., *Chemical Abstracts*, vol. 107 π46293 (1986).
Donescu–Stoian et al., *Chemical Abstracts*, vol. 72, #70612 (1969).
De Stevens et al., *Chemical Abstracts*, vol. 71, #53561 (1969)–(equivalent of US pat. #3,449,498, above).

*Primary Examiner*—Paul R. Michl
*Assistant Examiner*—William E. Benston
*Attorney, Agent, or Firm*—John W. Routh; Steven H. Flynn

[57] ABSTRACT

There is provided a pharmaceutically acceptable taste masking liquid excipient base for administration of relatively large amounts of unpleasant tasting medicines, said excipient base having higher than normal viscosities due to a combination of polyethylene glycol and cellulosic material.

44 Claims, No Drawings

TASTE MASKING LIQUIDS

CROSS-REFERENCE TO RELATED APPLICATIONS

This application is related to U.S. Ser. No. 08/380,867 filed Jan. 30, 1995, concurrently herewith.

BRIEF DESCRIPTION OF THE INVENTION

The present invention is directed to a pharmaceutically acceptable taste masking liquid excipient base for administration of a relatively large amount of unpleasant tasting medicines. More particularly, the taste masking effect is produced by increasing the viscosity of the liquid excipient base by adding to the liquid excipient base a viscosity increasing amount of a combination of a normally solid polyethylene glycol and sodium carboxymethyl cellulose.

The invention is further directed to medicinal compositions comprising the claimed liquid excipient base and said unpleasant tasting medicines.

Still further, the invention is directed to a method for taste masking unpleasant tasting medicines through their incorporation into the claimed liquid excipient bases.

BACKGROUND OF THE INVENTION

Pharmaceutically acceptable liquid excipient bases for administration of unpleasant tasting medicines are well known in the art. A typical system is described in U.S. Pat. No. 5,260,073 to Roger J. Phipps at column 7 as including a medicine, a solvent, a co-solvent, a buffer, a surfactant, a preservative, a sweetening agent, a flavoring agent, a dye or pigment, a viscosity modifier and water. The patent provides several examples of each ingredient in the system.

Although liquid excipient bases and their many ingredients are well known, unpleasant tasting medicines alone or in combination still present challenges to one skilled in the art to provide better taste masked products and, in certain instances, to provide taste masking for higher dosage amounts of unpleasant tasting medicines in smaller amounts of vehicle.

SUMMARY OF THE INVENTION

The present invention provides a pharmaceutically acceptable taste masking liquid excipient base for administration of relatively large amounts of unpleasant tasting pharmaceutically active compounds which liquid excipient base comprises polyethylene glycol having a molecular weight of at least 1000 and a cellulosic material, the spindle viscosity of the excipient base being between about 150 and about 1000 centipoises at 50 RPM.

The invention further provides pharmaceutically acceptable taste masking liquid excipient bases for administration of relatively large amounts of unpleasant tasting pharmaceutically active compounds.

Surprisingly, it has been found that the high viscosity liquid excipient base provides taste masking benefits to the extent that even extra strength formulations containing increased concentrations of adverse tasting pharmaceutically active compounds can be prepared. For example, guaifenesin, normally administered in dosages of no more than 100 milligrams in 5 milliliters of liquid, may be administered in dosages of 200 milligrams in the same volume of liquid without the patient experiencing an unduly adverse taste.

DETAILED DESCRIPTION OF THE INVENTION

The pharmaceutically acceptable taste masking bases useful in this invention are those having incorporated therein per 100 milliliters of liquid base about 5 to about 20 grams, preferably about 10 about 15 grams, of polyethylene glycol having an average molecular weight of about 950 about 2200, preferably about 1400 to about 1600, and a cellulosic material, the weight ratio of polyethylene glycol to the cellulosic material being between about 100:1 and about 20:1, such that the spindle viscosity is between about 150 and about 1000 centipoises at 50 RPM. These bases typically possess a spindle viscosity of about 150 to about 1200 centipoises when measured at 10 RPM. The higher viscosities of these bases are preferred for certain applications since such liquids are easier to pour from glass bottles and do not tend to spill from a spoon during their administration, especially to children.

The pH of the liquid base is from about 2.5 to about 5. At a lower pH, the cellulosic may tend to crystalize out, and at a higher pH, the taste worsens and preservatives must be used.

The polyethylene glycols useful in the practice of the present invention are those having an average molecular weight of about 950 to about 2200. Preferably, the polyethylene glycol has an average molecular weight of about 1400 to about 1600. Most preferably, the polyethylene glycol used in the practice of the present invention has an average molecular weight of about 1450. The use of mixtures of such polyethylene glycols is further within the practice of the present invention. As stated above, the polyethylene glycol component is used in amount of about 5 to about 20 grams, preferably about 10 to about 15 grams, per 100 milliliters of the liquid excipient base. The polyethylene glycol used in the specific examples was Polyethylene Glycol 1450 N.F. This polyethylene glycol, having a molecular weight of 1450 can be obtained from a number of suppliers. For instance, it is sold by Union Carbide Chemicals and Plastic Company, Inc. of Danbury, Conn. as CARBOWAX® 1450® and by Dow Chemical Company of Midland, Mich. as Dow Polyglycol E1450.

The cellulosic materials useful in the practice of the present invention are food grade materials and include methyl cellulose, hydroxyethylcellulose, hydroxypropylcellulose, hydroxyethyl methylcellulose, hydroxypropyl methylcellulose, carboxymethyl cellulose and mixtures thereof. Also useful are salts of such materials, such as the sodium salt of carboxymethyl cellulose, typically produced through the sodium hydroxide neutralization of a carboxylic acid derivative of cellulose. Preferred is the use of such dsodium salt of carboxymethyl cellulose. As stated above, such materials are used in amounts such that (a) the ratio of polyethylene glycol:cellulosic material is between about 100:1 and about 20:1, and (b) the spindle viscosity of the liquid excipent bases is between about 150 and about 1000 centipoise at 50 RPM. In a preferred embodiment of the present invention wherein the cellulosic material is the sodium salt of carboxymethylcellulose, such material is present in amounts between about 0.05 and about 0.6 grams, preferably between about 0.01 and about 0.5 grams, per 100 milliliters of the liquid excipient bases.

The cellulosic material used in the specific examples was HERCULES® Cellulose Gum 7MF which is the sodium salt of carboxymethylcellulose with a minimum purity of 99.5%, food grade, with a Type 7 Degree of Substitution and a medium viscosity range of 400–800 cps as a 2% by weight in water solution. The pharmaceutically active compounds and excipients other than the polyethylene glycol and the sodium carboxymethyl cellulose were of U.S.P. grade.

The pharmaceutically active compounds useful in the practice of the present invention include antihistamines, decongestants, antitussives, expectorants, non-steroidal anti-inflammatory drugs (NSAIDs) and other analgesic drugs such as acetominophen and phenacetin. These materials are incorporated into the claimed liquid excipient base in amounts governed by the solubility of the material in such excipient base and such that conventional dosages thereof shall be in compliance with applicable FDA regulations. For example, materials highly soluble in the liquid excipient base must not be incorporated to the extent that a typical dose (such as one teaspoon) contains more of such material than permitted by such regulations.

Among the antihistamines useful in the practice of the present invention (along with their preferred salt form) are chlorpheniramine (maleate), brompheniramine (maleate), dexchlorpheniramine (maleate), dexbrompheniramine (maleate), triprolidine (HCl), diphenhydramine (HCl), doxylamine (succinate), tripelennamine (HCl), cyproheptatine (HCl), bromodiphenhydramine (HCl), phenindamine (tartrate), pyrilamine (maleate, tannante) and azatadine (maleate).

The antitussives useful in the practice of the present invention (along with their preferred salt form) are caramiphen (edisylate), dextromethorphan (HBr) and codeine (phosphate, sulfate).

The decongestants useful in the practice of the present invention (along with their preferred salt form) are pseudoephedrine (HCl), phenylpropanolamine (HCl) and phenylephrine (bitartrate, tannate, HBr, HCl). Phenylpropanolamine (HCl) has been found to be unsuitable for use in the present invention if high fructose corn syrup sweetener is present. Therefore, if phenylpropanolamine HCl is used in conjunction with a sweetener, a sweetener such as sorbitol should be employed.

The expectorants useful in the practice of the present invention (along with their preferred salt form) are terpin hydrate, guaifenesin (glyceryl guaiacolate), potassium (iodide, citrate) and potassium guaicolsulfonate.

The non-steroidal anti-inflammatory drugs (NSAIDs) for use in the practice of the present invention may be selected from any of the following categories:

(1) propionic acid derivatives;

(2) acetic acid derivatives;

(3) fenamic acid derivatives;

(4) biphenylcarboxylic acid derivatives; and (5) oxicams.

Of the propionic acid derivatives for use herein, ibuprofen, naproxen, ketoprofen, flurbiprofen, fenoprofen, suprofen, fenbufen, and fluprofen may be mentioned as preferred compounds.

Of the acetic acid derivatives for use herein, tolmetin sodium, zomepirac, sulindac and indomethacin are included.

Of the fenamic acid derivatives for use herein, mefenamic acid and meclofenamate sodium are included.

Diflunisal and flufenisal are biphenylcarboxylic acid derivatives.

The oxicams include piroxicam, sudoxicam and isoxicam.

Of course, it will be appreciated by those skilled in the art, that any of the foregoing compounds may be utilized in the form of their pharmaceutically acceptable salt forms, e.g. $—COO^-Na^+$, $—COO^-K^+$, and the like.

Of the foregoing NSAIDs, ibuprofen and naproxen are the most preferred.

Other analgesic compounds useful in the practice of the present invention include acetominophen and phenacetin.

Of the pharmaceutically active compounds described above, those which are particularly preferred are set forth below along with preferred ranges for their inclusion into the claimed liquid excipient base.

Guaifenesin may be present in amounts of up to 300 milligrams per 5 mls. of the excipient base. Preferably, guaifenesin is present in amounts of about 10 to about 300 milligrams per 5 mls. of the excipient base. Most preferably, guaifenesin is present in amounts of about 100 to about 200 milligrams per 5 mls. of the excipient base.

Dextromethorphan may be present in amounts of between about 5 and about 20 milligrams per 5 mls. of the excipient base. Most preferably, dextromethorphan is present in amounts of about 10 to about 15 milligrams per 5 mls. of the excipient base.

Brompheniramine may be present in amounts of between about 0.5 and about 4.0 milligrams per 5 mls. of the excipient base. Most preferably, brompheniramine is present in amounts of about 2.0 milligrams per 5 mls. of the excipient base.

Pseudoephedrine may be present in amounts of between about 10 and about 60 milligrams per 5 mls. of the excipient base. Most preferably, pseudoephedrine is present in amounts of about 15 to about 30 milligrams per 5 mls. of the excipient base.

Acetaminophen may be present in amounts of up to about 200 milligrams per 5 mls. of the excipient base. Preferably, acetaminophen is present in amounts of about 50 to about 200 milligrams per 5 mls. of the excipient base. Most preferably, acetaminophen is present in amounts of about 150 to about 175 milligrams per 5 mls. of the excipient base.

Ibuprofen may be present in amounts of up to about 150 milligrams per 5 mls. of the excipient base. Preferably it is present in amounts of between about 50 and about 150 milligrams per 5 mls. of the excipient base. Most preferably, ibuprofen is present in amounts of about 100 milligrams per 5 mls. of the excipient base.

Naproxen may be present in amounts of about 50 to about 250 milligrams per 5 mls. of the excipient base. Preferably, it is present in amounts of between about 100 and about 150 milligrams per 5 mls. of the excipient base.

Excipients other than the polyethylene glycol and the sodium carboxymethyl cellulose useful in the practice of the present invention are those known to the art. These include humectants such as glycerin and propylene glycol, preservatives such sodium benzoate and paraben, sweeteners such as sodium saccharin, corn syrup and sorbitol solutions, menthol and various flavoring and coloring agents.

Although not willing to be bound thereby, it is believed that normally solid polyethylene glycol when melted and mixed with the propylene glycol, serves to solubilize the active ingredient and inhibits its crystallization at room temperature.

The invention will now be described with respect to the following specific examples.

EXAMPLE 1

The formulation of the invention set forth below was prepared in accordance with the following procedure. The example illustrates a formulation containing 200 milligrams of guaifenesin per 5 ml of formulation, double the normal amount, which has an acceptable taste.

| INGREDIENTS | AMT/5 ML | % | AMT/500 ML |
| --- | --- | --- | --- |
| GUAIFENESIN, USP | 200.0 MG | 4.0 | 20.0 g |
| DEXTROMETHORPHAN HBR, USP | 10.0 MG | 0.20 | 1.0 g |
| PSEUDOEPHEDRINE HCl, USP | 30.00 MG | 0.60 | 3.0 g |
| POLYETHYLENE GLYCOL 1450, NF | 500.00 MG | 10.00 | 50.0 g |
| PROPYLENE GLYCOL, USP | 0.75 ML | 15.00 | 75 ml |
| GLYCERIN, USP | 0.25 ML | 5.00 | 25 ml |
| HIGH FRUCTOSE CORN SYRUP 95 | 2.25 ML | 45.00 | 2 25 ml |
| SORBITOL SOLUTION, USP | 0.25 ML | 5.00 | 25 ml |
| l-MENTHOL, USP | 1.20 MG | 0.024 | 0.12 g |
| CITRIC ACID ANHYDROUS, USP | 45.00 MG | 0.90 | 4.5 g |
| SODIUM BENZOATE, USP | 5.00 MG | 0.10 | 0.5 g |
| SACCHARIN SODIUM, USP | 35.00 MG | 0.70 | 3.5 g |
| COLORING AND SWEETENER | 5.15 MG | 0.103 | 0.515 g |
| SODIUM CARBOXYMETHYLCELLULOSE 7MF, USP | 25.00 MG | 0.50 | 2.5 g |
| ART. FRUIT FLAVORS | 0.036 ML | 0.72 | 3.6 ml |
| PURIFIED WATER, USP QS TO | 5.00 ML | 100.0 | 500 ml |

The PEG 1450 was introduced into a flask and melted at 50°–60° c. and 62.5 ml of propyleneglycol was added with stirring. The guaifenesin, the dextromethorphan HBr and the pseudoephedrine HCl were then dissolved in the mixture. In a separate flask, the sodium CMC was dispersed in glycerin, and in a third flask, the sodium benzoate and sodium saccharin were dissolved in 60 ml of purified water. The sodium CMC dispersion was added to the third flask and stirred for at least 30 minutes or until the preparation becomes thick. The thick preparation was added to the bulk in the first flask. To the first flask were then added the sorbitol solution and the corn syrup with continuous stirring. The menthol was then dissolved in 12.5 ml of propylene glycol and added to the bulk. The citric acid was dissolved in 10 ml water and added to the bulk. The flavors and coloring were added and then purified water to 500 ml.

The resulting formulation has a pH of 3.38, 3.40, a spindle #3 viscosity at 10 RPM of 590 cps and a spindle viscosity at 50 rpm of 534 cps. The ratio of polyethylene glycol to sodium carboxymethylcellulose is 20:1.

The formulation has an acceptable flavor and taste.

EXAMPLE 2

The formulation of this example has the same proportions medicines and polyethylene glycol as in the previous example but only one fifth as much sodium CMC.

The procedure for this formulation was essentially the same as in the previous example except that the pseudoephedrine HCl was added with the citric acid dissolved in water and the coloring was separately added dissolved in water.

The resulting formulation had a pH of 3.509, a spindle #1 viscosity at 10 RPM of 236–256 cps and a spindle viscosity of 243–248 cps at 20 RPM. The ratio of polyethylene glycol to sodium carboxymethylcellulose is 100:1.

The formulation had an acceptable taste.

EXAMPLE 3

In this formulation only two medicines, guaifenisin and dextromethorpan HBr are used.

| INGREDIENTS | AMT/5 ML | % | AMT/1.0 L |
| --- | --- | --- | --- |
| GUAIFENESIN, USP | 200.0 MG | 4.0 | 40.0 g |
| DEXTROMETHORPHAN HBR, USP | 10.0 MG | 0.20 | 2.0 g |
| PSEUDOEPHEDRINE HCl, USP | 30.00 MG | 0.60 | 6.0 g |
| POLYETHYLENE GLYCOL 1450, NF | 500.00 MG | 10.00 | 100.0 g |
| PROPYLENE GLYCOL, USP | 0.75 ML | 15.00 | 150.0 ml |
| GLYCERIN, USP | 0.25 ML | 5.00 | 50.0 ml |
| HIGH FRUCTOSE CORN SYRUP 95 | 2.25 ML | 45.00 | 450.0 ml |
| SORBITOL SOLUTION, USP | 0.25 ML | 5.00 | 50.0 ml |
| l-MENTHOL, USP | 1.20 MG | 0.024 | 0.24 g |
| CITRIC ACID ANHYDROUS, USP | 25.00 MG | 0.5 | 5.0 g |
| SODIUM BENZOATE, USP | 7.5 MG | 0.15 | 1.5 g |
| SACCHARIN SODIUM, USP | 35.00 MG | 0.70 | 7.0 g |
| COLORING AND SWEETENER | 5.5 MG | 0.11 | 1.1 g |
| SODIUM CARBOXYMETHYLCELLULOSE 7MF, USP | 5.00 MG | 0.1 | 1.0 g |
| ARTIFICIAL FRUIT FLAVORS | 0.003 ML | 0.06 | 0.6 ml |
| PURIFIED WATER, USP QS TO | | | 1 L |

| INGREDIENTS | AMT/5 ML | % | AMT/1.0 L |
|---|---|---|---|
| GUAIFENESIN, USP | 200.0 MG | 4.0 | 40.0 g |
| DEXTROMETHORPHAN HBR, USP | 10.0 MG | 0.20 | 2.0 g |
| POLYETHYLENE GLYCOL 1450, NF | 500.00 MG | 10.00 | 100.0 g |
| PROPYLENE GLYCOL, USP | 0.75 ML | 15.00 | 150.0 ml |
| GLYCERIN, USP | 0.25 ML | 5.00 | 50.0 ml |
| HIGH FRUCTOSE CORN SYRUP 95 | 2.25 ML | 45.00 | 450.0 ml |
| SORBITOL SOLUTION, USP | 0.25 ML | 5.00 | 50.0 ml |
| l-MENTHOL, USP | 1.20 ML | 0.024 | 0.24 g |
| CITRIC ACID ANHYDROUS, USP | 30.0 MG | 0.6 | 6.0 g |
| SODIUM BENZOATE, USP | 7.5 MG | 0.15 | 1.5 g |
| SACCHARIN SODIUM, USP | 28.0 MG | 0.56 | 5.6 g |
| COLORING AND SWEETENER | 5.5 MG | 0.11 | 1.1 g |
| SODIUM CARBOXYMETHYLCELLULOSE 7MF, USP | 5.0 MG | 0.1 | 1.0 g |
| ART. FLAVORS | 0.003 ML | 0.06 | 0.6 ml |
| PURIFIED WATER, USP QS TO | 5.00 ML | 100.0 | 1.0 L |

The procedure for this formulation was essentially the same as in Example 2.

The resulting formulation has a pH of 3.45, 3.51, a spindle #1 viscosity at 10 RPM of 177 cps and a spindle viscosity at 20 RPM of 178 cps. which rose to 210 cps at both 10 RPM and 20 RPM within 24 hours. The ratio of polyethylene glycol to sodium carboxymethylcellulose is 100:1.

The formulation had an acceptable taste.

EXAMPLE 4

This formulation was similar to Example 2, except that the guaifenesin was 100 milligrams and the PEG content was 350 milligrams and shows that the PEG content must be coordinated with the sodium CMC content to achieve the proper viscosity.

The resulting formulation had a pH of 3.40, a spindle #1 viscosity at 10 RPM of 101 cps and a spindle #1 viscosity at 20 RPM of 102 cps. The ratio of polyethylene glycol to sodium carboxymethylcellulose is 70:1.

EXAMPLE 5

In this formulation similar to Example 2 only 100 milligrams of guaifenesin was employed, the polyethylene glycol was reduced to 350 milligrams and the sodium CMC was increased to 12.5 milligrams.

| INGREDIENTS | AMT/5 ML | % | AMT/1.0 L |
|---|---|---|---|
| GUAIFENESIN, USP | 100.0 MG | 2.0 | 200 g |
| DEXTROMETHORPHAN HBR, USP | 10.0 MG | 0.20 | 2.0 g |
| POLYETHYLENE GLYCOL 1450, NF | 350.0 MG | 7.00 | 70.0 g |
| PROPYLENE GLYCOL, USP | 0.75 ML | 15.00 | 150.0 ml |
| GLYCERIN, USP | 0.25 ML | 5.00 | 50.0 ml |
| HIGH FRUCTOSE CORN SYRUP 95 | 2.25 ML | 45.00 | 450.0 ml |
| SORBITOL SOLUTION, USP | 0.25 ML | 5.00 | 50.0 ml |
| l-MENTHOL, USP | 1.20 ML | 0.024 | 0.24 g |
| CITRIC ACID ANHYDROUS, USP | 25 MG | 0.5 | 5.0 g |
| SODIUM BENZOATE, USP | 7.5 MG | 0.15 | 1.5 g |
| SACCHARIN SODIUM, USP | 35.0 MG | 0.7 | 7.0 g |
| COLORING AND SWEETENER | 5.5 MG | 0.11 | 1.1 g |
| SODIUM CARBOXYMETHYLCELLULOSE 7MF, USP | 5.0 MG | 0.1 | 1.0 g |
| ART. FLAVORS | 0.003 ML | 0.06 | 0.6 ml |
| PURIFIED WATER, USP QS TO | | | 1 L |
| PSEUDOEPHEDRINE HCL, USP | 30.0 MG | 0.60 | 6.0 g |

The procedure for this formulation was essentially the same as in the previous example except that the pseudoephedrin HCl was dissolved with citric acid in water.

| INGREDIENTS | AMT/5 ML | % | AMT/1.0 L |
|---|---|---|---|
| GUAIFENESIN, USP | 100.0 MG | 2.0 | 20.0 g |
| DEXTROMETHORPHAN HBR, USP | 10.0 MG | 0.20 | 2.0 g |
| POLYETHYLENE GLYCOL 1450, NF | 350.0 MG | 7.00 | 70.0 g |
| PROPYLENE GLYCOL, USP | 0.75 ML | 15.00 | 150.0 ml |
| GLYCERIN, USP | 0.25 ML | 5.00 | 50.0 ml |
| HIGH FRUCTOSE CORN SYRUP 95 | 2.25 ML | 45.00 | 450.0 ml |

| INGREDIENTS | AMT/5 ML | % | AMT/1.0 L |
|---|---|---|---|
| SORBITOL SOLUTION, USP | 0.25 ML | 5.00 | 50.0 ml |
| l-MENTHOL, USP | 1.20 ML | 0.024 | 0.24 g |
| CITRIC ACID ANHYDROUS, USP | 25 MG | 0.5 | 5.0 g |
| SODIUM BENZOATE, USP | 7.5 MG | 0.15 | 1.5 g |
| SACCHARIN SODIUM, USP | 35.0 MG | 0.7 | 7.0 g |
| COLORING AND SWEETENER | 5.5 MG | 0.11 | 1.1 g |
| SODIUM CARBOXYMETHYLCELLULOSE 7MF, USP | 12.5 MG | 0.25 | 2.5 g |
| ART. FLAVORS | 0.003 | 0.06 | 0.6 ml |
| PURIFIED WATER, USP QS TO | | | 1 L |
| PSEUDOEPHEDRINE HCL, USP | 30.0 MG | 0.60 | 6.0 g |

The procedure for this formulation was essentially the same as Example 4.

The resulting formulation has a pH of 3.49, a spindle #1 viscosity at 10 RPM of 176 cps and a spindle viscosity at 20 RPM of 174 cps. The ratio of polyethylene glycol to sodium carboxymethylcellulose is 28:1.

The formulation had an acceptable taste.

EXAMPLE 6

In this experiment, the amount of guaifenesin was increased to 200 milligrams per 5 milliters and the amount of the other ingredients remained the same as in Example 5. The pH of the resulting formulation was 3.63 and the spindle #1 viscosity was 363 cps at 10 RPM and 357 cps at 20 RPM. The taste of the formulation was acceptable.

EXAMPLE 7

In this formulation similar to Example 3 only 100 milligrams of guaifenisin were employed, the polyethylene glycol was reduced to 350 milligrams and the sodium CMC was increased to 12.5 milligrams.

The resulting formulation has a pH of 3.45, a spindle #1 viscosity at 10 RPM of 202 cps and a spindle viscosity at 20 RPM of cps. The ratio of polyethylene glycol to sodium carboxymethylcellulose is 28:1.

The formulation has an acceptable taste.

EXAMPLE 8

In this formulation, acetominophen is present as the pharmaceutically active compound.

| INGREDIENTS | AMT/5 ML | % | AMT/1.0 L |
|---|---|---|---|
| GUAIFENESIN, USP | 100 MG | 2.0 | 20.0 g |
| DEXTROMETHORPHAN HBR, USP | 10.0 MG | 0.2 | 2.0 g |
| POLYETHYLENE GLYCOL 1450, NF | 350 MG | 7.0 | 70.0 g |
| PROPYLENE GLYCOL, USP | 0.75 ML | 15.0 | 150.0 ml |
| GLYCERIN, USP | 0.25 ML | 5.0 | 50.0 ml |
| HIGH FRUCTOSE CORN SYRUP 95 | 2.25 ML | 45.0 | 450 ml |
| SORBITOL SOLUTION, USP | 0.25 ML | 5.0 | 50 ml |
| l-MENTHOL, USP | 1.20 ML | 0.024 | 0.24 g |
| CITRIC ACID ANHYDROUS, USP | 30.0 MG | 0.6 | 6.0 g |
| SODIUM BENZOATE, USP | 7.5 MG | 0.15 | 1.5 g |
| SACCHARIN SODIUM, USP | 28.0 MG | 0.56 | 5.6 g |
| COLORING AND SWEETENER | 5.5 MG | 0.11 | 1.1 g |
| SODIUM CARBOXYMETHYLCELLULOSE 7MF, USP | 12.5 MG | 0.25 | 2.5 g |
| FLAVORS | 0.003 ML | 0.06 | 0.6 ml |
| PURIFIED WATER, USP QS TO | | | 1 L |

The procedure for this formulation was essentially the same as in Example 3.

| INGREDIENTS | AMT/5 ML | % | AMT/0.5 L |
|---|---|---|---|
| ACETOMINOPHEN, USP | 160.0 MG | 3.2 | 40.0 g |
| POLYETHYLENE GLYCOL 1450, NF | 500.00 MG | 10.00 | 50.0 g |
| PROPYLENE GLYCOL, USP | 0.75 ML | 15.00 | 75.0 ml |
| GLYCERIN, USP | 0.25 ML | 5.00 | 25.0 ml |
| HIGH FRUCTOSE CORN SYRUP 95 | 2.25 ML | 45.00 | 225.0 ml |

-continued

| INGREDIENTS | AMT/5 ML | % | AMT/ 0.5 L |
|---|---|---|---|
| SORBITOL SOLUTION, USP | 0.25 ML | 5.00 | 25.0 ml |
| 1-MENTHOL, USP | 1.20 ML | 0.024 | 0.12 g |
| CITRIC ACID ANHYDROUS, USP | 30.0 MG | 0.6 | 3.0 g |
| SODIUM BENZOATE, USP | 7.5 MG | 0.15 | 0.75 g |
| SACCHARIN SODIUM, USP | 28.0 MG | 0.56 | 2.8 g |
| COLORING AND SWEETENER | 5.5 MG | 0.11 | 0.55 g |
| SODIUM CARBOXYMETHYLCELLULOSE 7MF, USP | 5.0 MG | 0.1 | 0.5 g |
| PURIFIED WATER, USP QS TO | | | 500 ML |

The PEG 1450 was introduced into a flask and melted at 50°–60° c. and 60 ml. of the propylene glycol was added with stirring. The acetominophen was then added and dissolved in the mixture. In a separate flask, the sodium CMC was dispersed in glycerin, and in a third flask, the sodium benzoate and sodium saccharin were dissolved in 55 ml of purified water. The sodium CMC dispersion was added to the third flask and stirred for about 45 minutes or until the preparation became thick. The thick preparation was added to the bulk in the first flask (containing the acetominophen). To the first flask were then added the sorbitol solution and the corn syrup with continuous stirring. The menthol was then dissolved in 15.0 ml of propylene glycol and added to the bulk. The sweetener and coloring were added and then purified water added until the volume of the solution equaled 500 ml. Citric acid dissolved in 10 ml water was then added to the bulk until the pH was about 3.5.

The resulting formulation has a pH of 3.48 3.56, a spindle #3 viscosity at 10 RPM of 234 cps. The ratio of polyethylene glycol to sodium carboxymethylcellulose is 100:1.

The formulation has an acceptable flavor and taste.

EXAMPLE 9

The procedure of Example 8 was repeated except that 20.0 grams of acetominophen were used. This produced a composition containing 200 mg of acetominohen per 5 ml of the composition.

The resulting formulation has a pH of 3.45 3.51, a spindle #3 viscosity at 10 RPM of 256 c.p.s. The ratio of polyethylene glycol to sodium carboxymethylcellulose is 100:1.

The formulation has an acceptable flavor and taste.

We claim:

1. A pharmaceutical composition comprising (i) a liquid excipient base consisting essentially of water and per 100 milliliters of said base about 5 to about 20 grams of a (a) polyethylene glycol having a molecular weight of about 950 to about 2200, and (b) a cellulosic compound selected from the group consisting of methyl cellulose, hydroxyethycellulose, hydroxypropylcellulose, hydroxyethyl methylcellulose, hydroxyproply methylcellulose, carboxymethyl cellulose, mixtures and salts thereof, the weight ratio of said polyethylene glycol to said cellulosic compound being between about 100:1 and about 20:1, and the spindle viscosity of the liquid excipient base being between about 150 and about 1000 centipoises at 50 RPM and 150–1200 centipoises at 10 RPM, and (ii) at least one pharmaceutically active compound selected from the group consisting of antihistamines, decongestants, antitussives, expectorants, non-steroidal anti-inflammatory drugs (NSAIDs) and analgesic drugs, said pharmaceutically active compound being dissolved in the liquid excipient base.

2. The composition of claim 1 wherein the pharmaceutically active compound is an antihistamine selected from the group consisting of chlorpheniramine, brompheniramine, dexchlorpheniramine, dexbrompheniramine, triprolidine, diphenhydramine, doxylamine, tripelennamine, cyproheptatine, bromodiphenhydramine, phenindamine, pyrilamine and azatadine.

3. The composition of claim 1 wherein the pharmaceutically active compound is a decongestant selected form the group consisting of pseudoephedrine HCl, phenylpropanolamine and phenylephrine.

4. The composition of claim 3 wherein the pharmaceutically active compound is pseudoephedrine HCl in an amount of about 10 to about 60 milligrams per 5 milliliters of the excipient base.

5. The composition of claim 4 wherein the pharmaceutically active compound is pseudoephedrine HCl in an amount of about 15 to about 30 milligrams per 5 milliliters of the excipient base.

6. The composition of claim 1 wherein the pharmaceutically active compound is an expectorant selected from the group consisting of oterpin hydrate, guaifenesin, potassium iodide, potassium citrate and potassium guaicolsulfonate.

7. The composition of claim 6 wherein the expectorant is guaifenesin in an amount up to about 300 milligrams per 5 milliliters of the excipient base.

8. The composition of claim 7 wherein the guaifenesin is present in an amount of about 100 to about 200 milligrams per 5 milliliters of the excipient base.

9. The composition of claim 1 wherein the pharmaceutically active compound is an antitussive selected from the group consisting of caramiphen, dextromethorphan HBr, codeine phosphate and codeine sulfate.

10. The composition of claim 1 wherein the antitussive is dextromethorphan HBr in an amount of between about 5 and about 20 milligrams per 5 milliliters of excipient base.

11. The composition of claim 10 wherein the antitussive is dextromethorphan HBr in an amount of between about 10 and about 15 milligrams per 5 milliliters of excipient base.

12. The composition of claim 1 wherein the NSAID is selected from the group consisting of ibuprofen, ketoprofen and naproxen.

13. The composition of claim 12 wherein ibuprofen is present in in an amount ranging from about 50 to about 150 milligrams per 5 milliliters of excipient base.

14. The composition of claim 13 wherein ibuprofen is present in in an amount ranging from about 100 to about 150 milligrams per 5 milliliters of excipient base.

15. The composition of claim 12 wherein naproxen is present in in an amount ranging from about 50 to about 250 milligrams per 5 milliliters of excipient base.

16. The composition of claim 15 wherein naproxen is present in in an amount ranging from about 100 to about 150 milligrams per 5 milliliters of excipient base.

17. The composition of claim 1 wherein the analgesic is acetominophen.

18. The composition of claim 17 wherein acetominophen is present in an amount up to about 200 milligrams per 5 milliliters of the excipient base.

19. The composition of claim 18 wherein acetominophen is present in an amount of about 150 to about 175 milligrams per 5 milliliters of the excipient base.

20. A method for taste masking at least one unpleasant tasting pharmaceutically active compound comprising dissolving such unpleasant tasting pharmaceutically active compound into a liquid excipient base consisting essentially of water, polyethylene glycol having a molecular weight of about 950 to about 2200, and a cellulosic compound selected from the group consisting of methyl cellulose, hydroxyethylcellulose, hydroxypropylcellulose, hydroxyethyl methylcellulose, hydroxypropyl methylcellulose, carboxymethyl cellulose, mixtures and salts thereof, the spindle viscosity of the liquid excipient base being between about 150 and about 1000 centipoises at 50 RPM and 150–1200 centipoises at 10 RPM.

21. The method of claim 20 wherein wherein the polyethylene glycol has a molecular weight of between 1400 and about 1600.

22. The method of claim 20 wherein the weight ratio of polyethylene glycol and cellulosic compound is between about 100:1 and about 20:1.

23. The method of claim 20 wherein the cellulosic compound is sodium carboxymethyl cellulose.

24. The method of claim 23 wherein the weight ratio of polyethylene glycol and sodium carboxymethylcellulose is between about 100:1 and about 20:1.

25. The method of claim 20 wherein the excipient base has a pH of between about 2.5 and about 5.

26. The method of claim 20 wherein the pharmaceutically active compound is selected from the group consisting of antihistamines, decongestants, antitussives, expectorants, non-steroidal anti-inflammatory drugs (NSAIDs) and analgesic drugs.

27. The method of claim 20 wherein the pharmaceutically active compound is an antihistamine selected from the group consisting of chlorpheniramine, brompheniramine, dexchlorpheniramine, dexbrompheniramine, triprolidine, diphenhydramine, doxylamine, tripelennamine, cyproheptatine, bromodiphenhydramine, phenindamine, pyrilamine and azatadine.

28. The method of claim 20 wherein the pharmaceutically active compound is a decongestant selected from the group consisting of pseudoephedrine HCl, phenylpropanolamine and phenylephrine.

29. The method of claim 28 wherein the pharmaceutically active compound is pseudoephedrine HCl in an amount of about 10 to about 60 milligrams per 5 milliliters of the excipient base.

30. The method of claim 29 wherein the pharmaceutically active compound is pseudoephedrine HCl in an amount of about 15 to about 30 milligrams per 5 milliliters of the excipient base.

31. The method of claim 20 wherein the pharmaceutically active compound is an expectorant selected from the group consisting of oterpin hydrate, guaifenesin, potassium iodide, potassium citrate and potassium guaicolsulfonate.

32. The method of claim 31 wherein the expectorant is guaifenesin in an amount up to about 300 milligrams per 5 milliliters of the excipient base.

33. The method of claim 32 wherein the guaifenesin is present in an amount of about 100 to about 200 milligrams per 5 milliliters of the excipient base.

34. The method of claim 20 wherein the pharmaceutically active compound is an antitussive selected from the group consisting of caramiphen, dextromethorphan HBr, codeine phosphate and codeine sulfate.

35. The method of claim 34 wherein the antitussive is dextromethorphan HBr in an amount of between about 5 and about 20 milligrams per 5 milliliters of excipient base.

36. The method of claim 34 wherein the antitussive is dextromethorphan HBr in an amount of between about 10 and about 15 milligrams per 5 milliliters of excipient base.

37. The method of claim 20 wherein the NSAID is selected from the group consisting of ketoprofen, ibuprofen and naproxen.

38. The method of claim 37 wherein ibuprofen is present in in an amount ranging from about 50 to about 150 milligrams per 5 milliliters of excipient base.

39. The method of claim 38 wherein ibuprofen is present in in an amount ranging from about 100 to about 150 milligrams per 5 milliliters of excipient base.

40. The method of claim 37 wherein naproxen is present in in an amount ranging from about 50 to about 250 milligrams per 5 milliliters of excipient base.

41. The method of claim 40 wherein naproxen is present in in an amount ranging from about 100 to about 150 milligrams per 5 milliliters of excipient base.

42. The method of claim 20 wherein the analgesic is acetominophen.

43. The method of claim 42 wherein acetominophen is present in an amount up to about 200 milligrams per 5 milliliters of the excipient base.

44. The method of claim 42 wherein acetominophen is present in an amount of about 150 to about 175 milligrams per 5 milliliters of the excipient base.

* * * * *